US005766520A

United States Patent [19]

Bronshtein

[11] Patent Number: 5,766,520

[45] Date of Patent: Jun. 16, 1998

[54] PRESERVATION BY FOAM FORMATION

[75] Inventor: Victor Bronshtein, Rochester, N.Y.

[73] Assignee: Universal Preservation Technologies, Inc., San Diego, Calif.

[21] Appl. No.: 785,473

[22] Filed: Jan. 17, 1997

Related U.S. Application Data

[60] Provisional application No. 60/021,796, Jul. 18, 1996.

[51] Int. Cl.[6] .......... B01J 13/00; B01J 13/02; B01J 13/04; B32B 5/16

[52] U.S. Cl. .......... 264/4.6; 264/4.1; 252/307; 252/315.3; 428/402.2; 424/45; 436/17; 436/18

[58] Field of Search .......... 252/307, 315.3; 364/4.1, 4.6; 428/402.2; 424/45; 436/17, 18

[56] References Cited

U.S. PATENT DOCUMENTS

| | | | |
|---|---|---|---|
| 4,891,319 | 1/1990 | Roser | 435/188 |
| 5,098,893 | 3/1992 | Franks et al. | 514/54 |
| 5,271,881 | 12/1993 | Redding, Jr. | 264/432 |
| 5,290,765 | 3/1994 | Wettlaufer et al. | 514/23 |
| 5,409,703 | 4/1995 | McAnalley et al. | 424/435 |
| 5,565,318 | 10/1996 | Walker et al. | 435/4 |

FOREIGN PATENT DOCUMENTS 0520748 12/1992 European Pat. Off. .

*Primary Examiner*—Nathan M. Nutter
*Attorney, Agent, or Firm*—Webb Ziesenheim Bruening Logsdon Orkin & Hanson, P.C.

[57] ABSTRACT

A method of preserving sensitive biological dispersions, suspensions, emulsions and solutions by forming stable foams from fluid materials to be dehydrated, as an aid both to the drying of one or more biologically active substrates in the fluid and as an aid in preparing an easily divisible dried product suitable for further commercial use. The stable foams are formed by partially removing the water to form a viscous liquid and by further subjecting the reduced liquid to vacuum, to cause it to "boil" during further drying at temperatures substantially lower than 100 degrees C. In other words, reduced pressure is applied to viscous solutions or suspensions of biologically active materials to cause the solutions or suspensions to foam during boiling, and during the foaming process further solvent removal causes the ultimate production of a stable open-cell or closed-cell foam.

14 Claims, No Drawings

PRESERVATION BY FOAM FORMATION

This application claims priority from Provisional patent application Ser. No. 60/021,796 filed Jul. 18, 1996.

FIELD OF THE INVENTION

The invention relates to methods for preserving sensitive biologically active solutes and suspensions, emulsions and dispersions of, for example, enzymes, proteins, viruses, serums, vaccines, liposomes and cell suspensions.

BACKGROUND OF THE INVENTION

The long-term storage of biologically active materials poses a unique challenge, considering that biologically active material may be the most fragile and environmentally vulnerable construct on our planet—by its very nature. Certainly very few hydrated materials are sufficiently stable to allow them to be isolated, purified and stored in room temperature solution for anything more than a very short period of time.

Both commercially and practically, storage of biologically active materials in dry form carries with it enormous benefits. Successfully dried reagents, materials and tissues have reduced weight and require reduced space for storage notwithstanding their increased shelf life. Room temperature storage of dried materials is moreover cost effective when compared to low temperature storage options and the concomitant cost.

Current technologies for producing dried biologically active materials include primarily spray-drying (see U.S. Pat. No. 5,565,318 directed to a variant of this) and fluidized bed drying, inasmuch as simple drying is virtually impossible to scale up to anything resembling a commercially useful scale. Reduced temperature preservation methods which may include a dehydration aspect include freeze-drying and/or cryogenic freezing. Freeze-drying is not well suited for the preservation of sensitive biologically active materials because ice crystal formation causes freeze-induced cryoinjury and is very costly.

Among the various protocols in which biologically active materials are transmuted to dry but still reversible to biologically active form, the particular problem persists in that simple air or vacuum drying procedures are extremely difficult to scale up. Drying is a diffusion limited process, so removal of the aqueous component becomes more challenging with respect to amounts in excess of about 10 microliters, for one thing, and the larger the substrate to be dried the more difficult it becomes to effect drying at its center. Time of drying is inversely proportional to the diffusion coefficient of water and proportional to the square of the sample size. Recourse to spray drying techniques is not always possible because the high temperatures typical of some of these can be damaging to delicate biologically active materials. Moreover, preparation of dried materials by known drying techniques can sometimes lead to dense, difficult to dissolve masses which do not lend themselves well to further handling in full-scale commercial biological and pharmaceutical applications.

A need therefore remains for a scalable method of preserving sensitive biologically active materials by drying.

SUMMARY OF THE INVENTION

In order to meet this need, the present invention is a method of preserving sensitive biological suspensions and solutions by forming stable foams from fluid materials to be dried, as an aid both to the drying of one or more biologically active substrates in the fluid and as an aid in preparing an easily soluble dried product suitable for further commercial use. The stable foams are formed by partially removing water in the biologically active sample to form a viscous liquid and by further subjecting the reduced liquid to vacuum to cause it to "boil" during further drying at temperatures substantially lower than 100 degrees C. In other words, reduced pressure is applied to viscous solutions or suspensions of biologically active materials to cause the solution or suspension to foam during boiling, and during the foaming process further water removal causes the ultimate production of a stable open-cell or closed-cell foam. Such foams are easily divisible by cutting, milling or other dividing techniques, and the foaming action itself enhances water removal by maximizing liquid surface area available for evaporation or other solvent evolution.

DETAILED DESCRIPTION OF THE INVENTION

The present invention is a method of preserving sensitive biological dispersions, suspensions, emulsions and solutions by forming stable foams from fluid materials to be dried, as an aid both to the drying of one or more biologically active substrates in the fluid and as an aid in preparing an easily divisible dried product suitable for further commercial use. The stable foams are formed by partially removing the water to form a viscous liquid and by further subjecting the reduced liquid to vacuum, to cause it to "boil" during further drying at temperatures substantially lower than 100 degrees C. In other words, reduced pressure is applied to viscous solutions or suspensions of biologically active materials to cause the solutions or suspensions to foam during boiling, and during the foaming process further solvent removal causes the ultimate production of a stable open-cell or closed-cell foam. Such foams are easily divisible by cutting, milling or other dividing techniques, and the foaming action itself enhances water removal by maximizing liquid surface area available for evaporation. (In general, the solvent fraction of the materials to be dried will be aqueous, however, it should be understood that the present method may be applied to solutions and suspensions of various types including those containing nonaqueous solvents or mixture of such solvents.)

Once the invention of combining drying protocols by boiling with reduced pressure is appreciated, it may be seen that in its simplest embodiments the inventive apparatus is a novel combination of a vacuum pump with a temperature controlled desiccator device. Optional features of such a combination include sensors for temperature measurement and heat flow control, microprocessors for calculating other process parameters based on data collected from these and other sensors and etc. Such a device allows implementation of a novel two-dimensional vacuum and temperature protocol for drying.

The biological liquids to which this vacuum-boiling-foam-forming innovation can be applied are virtually endless. Literally any solution or suspension can be dehydrated using the vacuum boiling procedure of the invention, although the method has clear advantages (i.e., damage avoidance due to lower drying temperatures) in the preservation of biologically sensitive materials. Solutions incorporating vitrifying enhancers and other protectants, as well as solvents of virtually any type, will undergo enhanced drying when subjected to sub-atmospheric pressure and foam formation during the boiling process. Protectants can include, without limitation, sugars (including sucrose among others), carbohydrates, polysaccharides, water-soluble polymers, peptides or proteins as long as the protectant enhances the ability of the biologically active material to withstand drying and storage and does not interfere with the particular biological activity.

In an important embodiment of the invention, the foam forming process includes two steps: (a) an intensive dehydration of the solution or dispersion containing the biologically active agent by boiling under vacuum, to form a stable, non-collapsing foam and (b) subsequent secondary drying of the foams, to the extent that the foams are stable and do not collapse during storage.

As noted above, the invention provides a scalable method for preserving sensitive biologically active materials (proteins, enzymes, serums, vaccines, viruses, liposomes and cell suspensions) with a uniquely engineered drying method. Using this method, it is possible to rehydrate the samples with water or aqueous solutions to reverse the process to the initial biological activity. The method may be applied for the preservation of pharmaceutical, fluid or virtually any other biologically active products or solutes.

In the method of the invention, relatively large amounts of biologically active liquids (solutions or suspensions) are dehydrated by boiling under vacuum to form stable foams. Formation of foams is a kinetic process and depends on the rate of temperature and vacuum changes during formation of the foam as well as the initial concentration and composition of the solution or dispersion containing the biologically active substance. Stability of the foams may be further enhanced by the addition of surfactants or other synthetic or biological polymers as long as those additives do not interfere with the biological activity of the solute intended for conversion to dry form. Secondary drying and optional cooling of the formed and initially dry foams may be conducted to assure stability of the foam during storage. Cooling may be used to convert the foamed material to the glass state. Foams prepared according to the present invention may be stored whole or subdivided or milled, and when they are to be used need only be rehydrated in order to restore their original biologic activity.

The following Examples are illustrative.

EXAMPLE 1

Aqueous 50% glycerol isocitrate dehydrogenase solution from Sigma Chemical Co. containing 59.4 units of activity per ml. was dialyzed for 5 hours in 0.1M TRIS HCl buffer (pH=7.4). The activity of the isocitrate dehydrogenase in the 0.1M TRIS HCl solution after dialysis was 26+/−1.8 units per ml. The activity decrease was associated with decrease in the enzyme concentration because of dilution during the dialysis.

One hundred (100) microliters of the mixture containing 50 microliters of 50% by weight sucrose solution and 50 microliters of the isocitrate dehydrogenase suspension in 0.1M TRIS HCl buffer (pH=7.4) was placed in 1.5 ml. plastic tubes and preserved by drying at room temperature. First, the samples were dried 4 hours under low vacuum (hydrostatic pressure P=0.2 atm). Second, the samples were boiled during 4 hours under high vacuum of (P<0.01 atm). During this step a stable dry foam was formed in the tubes. Third, the samples were stored during 8 days over DRIERITE under vacuum at room temperature.

After the days of storage, the samples were rehydrated with 500 microliters water. Rehydration of the samples containing dry foams was an easy process that was completed within several seconds. Reconstituted sample was assayed for activity by assaying ability to reduce NADP, measured spectrophotometrically at 340 nm. The reaction mix included: 2 ml. 0.1M TRIS HCl buffer, pH=7.4; 10 microliters of 0.5% by weight NADP+; 10 microliters of 10 mM solution of $MnSO_4$; 10 microliters of 50 mM 1-isocitrate; and 10 microliters of an isocitrate dehydrogenase solution. The activity was 2.6+/−0.2 units/ml. which means there was no loss of activity during drying and subsequent storage at room temperature.

EXAMPLE 2

One Hundred (100) microliters of a mixture containing 50 microliters of 50% by weight sucrose solution and 50 microliters of an ice nucleating bacteria suspension supplied by Genencor International, Inc. were placed in 1.5 ml. plastic tubes and preserved by drying at room temperature. First, the samples were dried for 4 hours under low vacuum (hydrostatic pressure P=0.2 atm). Second, the samples were boiled during 4 hours under high vacuum (P<0.01 atm). After boiling under vacuum, a stable dry foam was formed in the tubes. Third, the samples were stored during 8 days over DRIERITE under vacuum at room temperature. After 8 days of storage the samples were rehydrated with 500 microliters water. Rehydration of the samples containing the dry foams was an easy process that was completed within several seconds. Then the samples were assayed for ice nucleation activity in comparison with control samples. We found that there was no significant difference between the ice nucleating activity per 1,000 bacteria in the samples preserved by the present method versus the control samples.

Although the invention has been described with reference to particular embodiments and details above, the invention is only to be limited insofar as is set forth in the accompanying claims.

I claim:

1. A method of shelf preservation of biologically active materials by drying comprising the step of subjecting a solution, dispersion or suspension containing a biologically active agent to a vacuum corresponding to the remaining hydrostatic pressure lower than 24 Torr sufficient to cause said solution, dispersion or suspension to boil such that said boiled solution, dispersion or suspension is dried to yield a mechanically stable foam during boiling.

2. The method according to claim 1 wherein said hydrostatic pressure is between 0 and 7.6 Torr.

3. The method according to claim 1 wherein prior to the step of subjecting said solution, dispersion or suspension to a high vacuum said solution, dispersion or suspension is dehydrated or concentrated by evaporation from liquid state at a low vacuum corresponding to the remaining hydrostatic pressure higher than 7.6 Torr or by evaporation from partially frozen state or by concentration by reverse osmosis or other membrane technologies to reduce the time during which said high vacuum must be applied and to increase the viscosity of said solution, dispersion or suspension before boiling under high vacuum.

4. The method according to claim 1 wherein a secondary drying process is carried out by applying one of a vacuum or dry air to said stable foam at elevated temperature.

5. The method according to claim 4 wherein after the secondary drying procedure the foam is cooled to a temperature that is lower than the glass transition temperature of the dried foam.

6. The method according to claim 5 wherein a surfactant is added to said solution, dispersion or suspension prior to application of said high vacuum to enhance foam stability during secondary drying.

7. The method according to claim 6 wherein said solution, dispersion or suspension contains a protectant selected from the group consisting of a sugar, carbohydrate, polysaccharide, polymer, peptide, protein and a mixture thereof, wherein said protectant enhances the ability of the biologically active material to withstand drying and storage.

8. The method according to claim 1 wherein said process further includes the step of rehydrating said stable foam by contacting said foam with a suitable solvent.

9. The method according to claim 8 wherein said rehydration is performed at a temperature higher than the temperature in which the foam was stored prior to rehydration.

10. The method according to claim 9 wherein the temperature in which the foam was stored prior to rehydration is at least as high as ambient temperature.

11. The method according to claim 8 wherein said rehydration is performed at a temperature the same or lower than the temperature in which the foam was stored prior to rehydration.

12. The method according to claim 8 wherein the temperature in which the foam was stored prior to rehydration is lower than or equal to ambient temperature.

13. The method according to claim 8 wherein said solvent is an aqueous solution including a cryoprotectant.

14. The method according to claim 7 wherein said sugar is sucrose.

* * * * *

UNITED STATES PATENT AND TRADEMARK OFFICE
CERTIFICATE OF CORRECTION

PATENT NO. : 5,766,520
DATED : June 16, 1998
INVENTOR(S) : Victor Bronshtein

It is certified that error appears in the above-identified patent and that said Letters Patent is hereby corrected as shown below:

Title Page, [60] Related U.S. Application Data, refer to date, "Jul. 18, 1996" should read --Jul. 15, 1996--.

Column 1 Line 4 "Jul. 18, 1996" should read --Jul. 15, 1996--.

Signed and Sealed this

Twenty-second Day of September, 1998

*Attest:*

BRUCE LEHMAN

*Attesting Officer*

*Commissioner of Patents and Trademarks*

Adverse Decision In Interference

Patent No. 5,766,520, Victor Bronshtein, PRESERVATION BY FOAM FORMATION, Interference No. 104,727, final judgment adverse to the patentees rendered March 3, 2003, as to claims 1-14.

*(Official Gazette July 29, 2003)*